(12) United States Patent
Palermo et al.

(10) Patent No.: US 6,627,635 B2
(45) Date of Patent: Sep. 30, 2003

(54) METHOD OF PREVENTING ABUSE OF OPIOID DOSAGE FORMS

(75) Inventors: Philip J. Palermo, Bethel, CT (US); Robert F. Kaiko, Weston, CT (US); Robert D. Colucci, Newtown, CT (US)

(73) Assignee: Euro-Celtique S.A., Luxembourg (LU)

( * ) Notice: Subject to any disclaimer, the term of this patent is extended or adjusted under 35 U.S.C. 154(b) by 0 days.

(21) Appl. No.: 09/815,162

(22) Filed: Mar. 22, 2001

(65) Prior Publication Data

US 2002/0004509 A1 Jan. 10, 2002

Related U.S. Application Data

(63) Continuation of application No. 09/218,663, filed on Dec. 22, 1998, now Pat. No. 6,228,863.
(60) Provisional application No. 60/068,479, filed on Dec. 22, 1997.

(51) Int. Cl.[7] ............................................. A61K 31/44
(52) U.S. Cl. .................... 514/282; 514/289; 514/810; 514/812
(58) Field of Search ............................. 514/282, 289, 514/810, 812

(56) References Cited

U.S. PATENT DOCUMENTS

| | | | |
|---|---|---|---|
| 2,770,569 A | 11/1956 | Fromherz et al. ............. 167/65 |
| 3,332,950 A | 7/1967 | Blumberg et al. ........... 260/285 |
| 3,493,657 A | 2/1970 | Lewenstein et al. ........ 424/260 |
| 3,676,557 A | 7/1972 | Lachman et al. ............ 424/260 |
| 3,773,955 A | 11/1973 | Pachter et al. .............. 424/260 |
| 3,879,555 A | 4/1975 | Pachter et al. .............. 424/260 |
| 3,966,940 A | 6/1976 | Pachter et al. .............. 424/260 |
| 4,176,186 A | 11/1979 | Goldberg ..................... 424/260 |
| 4,401,672 A | 8/1983 | Portoghese ................. 424/260 |
| 4,451,470 A | 5/1984 | Ganti ........................ 424/260 |
| 4,457,933 A | 7/1984 | Gordon et al. .............. 424/260 |
| 4,464,378 A | 8/1984 | Hussain ...................... 424/260 |
| 4,573,995 A | 3/1986 | Chen et al. .................. 604/896 |
| 4,582,835 A | 4/1986 | Lewis et al. ................ 514/282 |
| 4,608,376 A | 8/1986 | Pasternak .................... 514/282 |
| 4,661,492 A | 4/1987 | Lewis et al. ................ 514/282 |
| 4,719,215 A | 1/1988 | Goldberg ..................... 514/282 |
| 4,730,048 A | 3/1988 | Portoghese et al. ........... 546/45 |
| 4,760,069 A | 7/1988 | Rzeszotarski et al. ....... 514/282 |
| 4,769,372 A | 9/1988 | Kreek et al. ................ 514/282 |
| 4,785,000 A | 11/1988 | Kreek et al. ................ 514/282 |
| 4,803,208 A | 2/1989 | Pasternak .................... 514/282 |
| 4,806,341 A | 2/1989 | Chien et al. ................. 424/448 |
| 4,806,543 A | 2/1989 | Choi .......................... 514/464 |
| 4,806,558 A | 2/1989 | Wuest et al. ................ 514/381 |
| 4,861,781 A | 8/1989 | Goldberg ..................... 514/282 |
| 4,873,076 A | 10/1989 | Fishman et al. .............. 424/10 |
| 4,882,335 A | 11/1989 | Sinclair ...................... 514/282 |
| 4,889,860 A | 12/1989 | Rzeszotarski et al. ....... 514/282 |
| 4,935,428 A | 6/1990 | Lewis ......................... 514/282 |
| 5,075,341 A | 12/1991 | Mendelson et al. .......... 514/282 |
| 5,086,058 A | 2/1992 | Sinclair et al. .............. 514/282 |
| 5,096,715 A | 3/1992 | Sinclair ...................... 424/449 |
| 5,102,887 A | 4/1992 | Goldberg ..................... 514/282 |
| 5,149,538 A | 9/1992 | Granger et al. .............. 424/449 |
| 5,225,440 A | 7/1993 | London et al. .............. 514/535 |
| 5,236,714 A | 8/1993 | Lee et al. .................... 424/449 |
| 5,256,669 A | 10/1993 | Askanazi et al. ............ 514/282 |
| 5,316,759 A | 5/1994 | Rose et al. ................... 424/10 |
| 5,317,022 A | 5/1994 | Borsodi et al. .............. 514/282 |
| 5,321,012 A | 6/1994 | Mayer et al. ................. 514/25 |
| 5,352,680 A | 10/1994 | Portoghese et al. .......... 514/279 |
| 5,352,683 A | 10/1994 | Mayer et al. ................ 514/289 |
| 5,356,900 A | 10/1994 | Bihari et al. ................ 514/282 |
| 5,376,662 A | 12/1994 | Ockert ........................ 514/282 |
| 5,426,112 A | 6/1995 | Zagon et al. ................. 514/282 |
| 5,457,208 A | 10/1995 | Portoghese et al. ........... 546/35 |
| 5,472,943 A | 12/1995 | Crain et al. .................. 514/12 |
| 5,486,362 A | 1/1996 | Kitchell et al. .............. 424/426 |
| 5,502,058 A | 3/1996 | Mayer et al. ................ 514/289 |
| 5,512,578 A | 4/1996 | Crain et al. .................. 514/282 |
| 5,514,680 A | 5/1996 | Weber et al. ................ 514/249 |
| 5,534,492 A | 7/1996 | Aston et al. ................ 514/608 |
| 5,556,838 A | 9/1996 | Mayer et al. ................. 514/25 |
| 5,574,052 A | 11/1996 | Rose et al. .................. 514/343 |
| 5,578,725 A | 11/1996 | Portoghese et al. ........... 546/35 |
| 5,580,876 A | 12/1996 | Crain et al. ................. 514/282 |

(List continued on next page.)

FOREIGN PATENT DOCUMENTS

| | | | |
|---|---|---|---|
| DE | 2222039 | 11/1972 | .......... A61K/27/00 |
| DE | 4325465 | 2/1995 | .......... A61K/31/485 |
| DE | 29719704 | 2/1997 | .......... A61K/31/485 |
| DE | 19651551 | 6/1998 | .......... A61K/31/485 |
| EP | 0352361 | 1/1990 | .......... A61K/31/485 |
| EP | 0913152 | 6/1999 | .......... A61K/31/485 |
| WO | WO8303197 | 9/1983 | ............ A61K/9/22 |
| WO | WO9406426 | 3/1994 | .......... A61K/31/46 |
| WO | WO9503804 | 2/1995 | .......... A61K/31/485 |
| WO | WO96/02251 | 2/1996 | .......... A61K/31/485 |
| WO | WO9733566 | 9/1997 | ............ A61K/9/20 |
| WO | WO9835679 | 8/1998 | .......... A61K/31/485 |

OTHER PUBLICATIONS

Sunshine, et al., "Analgesic Efficacy of Pentazocine Versus a Pentazocine–Naloxone Combination Following Oral Administration", Clin. J. Pain 1988; 4:35–40.

(List continued on next page.)

*Primary Examiner*—Kevin E. Weddington
(74) *Attorney, Agent, or Firm*—Davidson, Davidson & Kappel, LLC

(57) ABSTRACT

The invention relates in part to a method of reducing the abuse potential of an oral dosage form of an opioid analgesic, wherein an analgesically effective amount of an orally active opioid agonist is combined with an opioid antagonist into an oral dosage form which would require at least a two-step extraction process to be separated from the opioid agonist, the amount of opioid antagonist including being sufficient to counteract opioid effects if extracted together with the opioid agonist and administered parenterally.

23 Claims, No Drawings

U.S. PATENT DOCUMENTS

| | | | |
|---|---|---|---|
| 5,585,348 A | 12/1996 | Crain et al. | 514/12 |
| 5,616,601 A | 4/1997 | Khanna et al. | 514/399 |
| 5,624,932 A | 4/1997 | Qin et al. | 514/282 |
| 5,633,259 A | 5/1997 | Qin et al. | 514/282 |
| 5,767,125 A | 6/1998 | Crain et al. | 514/282 |
| 5,858,017 A | 1/1999 | Demopulos et al. | 604/890.1 |
| 5,860,950 A | 1/1999 | Demopulos et al. | 804/49 |
| 5,866,164 A | 2/1999 | Kuczynski et al. | 424/472 |
| 5,880,132 A | 3/1999 | Hill | 514/282 |
| 5,972,954 A | 10/1999 | Foss | 514/282 |
| 6,228,863 B1 * | 5/2001 | Palermo et al. | 514/282 |
| 6,277,384 B1 | 8/2001 | Kaiko et al. | 424/400 |

OTHER PUBLICATIONS

Wang, et al., "Crossover and Parallel Study of Oral Analgesics". J. Clin. Phamacol 1981; 21:162–8.

Gonzalez JP, et. al., Naltrexone: A review of its Phamacodynamic and Pharmacokinetic Properties and Therapeutic Efficacy in the Management of Opioid Dependence. Drugs 1988; 35:192–213.

Weinhold, LL, et al., Buprenorphine Alone and in Combination with Naltrexone in Non–Dependent Humans, Drug and Alcohol Dependence 1992; 30:263–274.

Mendelson J., et al., Buprenorphine and Naloxone Interactions in Opiate–Dependent Volunteers, Clin. Phar. Ther. 1996; 60:105–114.

Physician's Desk Reference 48th ed., 1994; 2120–2121, Montvale, NJ.

Crain, et al., "Ultra–low concentrations of naloxone selectivity antagonize excitory effects of morphine on sensory neurons, thereby increasing its antinociceptive potency and attentuating tolerance/dependence during chronic cotreatment", Proc. Natl. Acad. Sci. USA, 1995; vol. 92, 10540–10544.

Shen, et al., "Ultra–low doses of naltrexone or etorphine increase morphin's antinociceptive potency and attenuate tolerance/dependence in mice", Brain Research, 757:176–190 (1997).

Holmes, et al., Anesth. Analg. 77:1166–73 (1993).

Miaskowski, et al., Brain Research 596:41–45 (1992).

Vaccarino, et al., Pain 36:103–109 (1989).

Cappel, et al., Pharmacology Biochemistry & Behavior, vol. 34, pp. 425–427 (1989).

Gan et al., "Opioid–sparing Effects of a Low–dose Infusion of Naloxone in Patient–administered Morphine Sulfate.", Anesthesiology, vol. 87(5), (1997) pp. 1075–1080.

Translation of previously submitted German patent application DE 43 25 465.

Hanson, Analgesic, Antipyretic and Anti–inflammatory Drugs in Remington's Science and Practice of Pharmacy vol. 2, 1995, 1207.

Yuan et al., Drug and Alcohol Dependence 52 (1998) 161–165.

Yuan et al., Clinical Trials and Therapeutics, 61 (Apr. 1997) 467–475.

Foss et al., J. Clin Pharmacol 33 (1993) 747–751.

Abstract, Cancer Chemother Pharmacol 1988; 42(4):287–91.

Walsh et al., Effect of Naltrexone on Response to Intravenous Cocaine, Hydromorphone, and their combination in humans, CAPLUS, 1996:702346.

* cited by examiner

METHOD OF PREVENTING ABUSE OF OPIOID DOSAGE FORMS

BACKGROUND OF THE INVENTION

This application is a continuation of U.S. patent application Ser. No. 09/218,663, filed Dec. 22, 1998 now U.S. Pat. No. 6,228,863, which claims priority from U.S. Provisional Application Ser. No. 60/068,479, filed Dec. 22, 1997, hereby incorporated by reference.

Opioids, also known as opioid agonists, are a group of drugs that exhibit opium or morphine-like properties. The opioids are employed primarily as moderate to strong analgesics, but have many other pharmacological effects as well, including drowsiness, respiratory depression, changes in mood and mental clouding without a resulting loss of consciousness. Opioids act as agonists, interacting with stereospecific and saturable binding sites in the brain and other tissues. Endogenous opioid-like peptides are present particularly in areas of the central nervous system that are presumed to be related to the perception of pain; to movement, mood and behavior, and to the regulation of neuroendocrinological functions. Opium contains more than twenty distinct alkaloids. Morphine, codeine and papaverine are included in this group.

By the middle of the nineteenth century, the use of pure alkaloids such as morphine rather than crude opium preparations began to spread throughout the medical world. Parenteral use of morphine tended to produce a more severe variety of compulsive drug use. The problem of addiction to opioids stimulated a search for potent analgesics that would be free of the potential to produce addiction. By 1967, researchers had concluded that the complex interactions among morphine-like drugs, antagonists, and what was then called "mixed agonist-antagonist" could best be explained by postulating the existence of more than one type of receptor for opioids and related drugs. With the advent of new totally synthetic entities with morphine-like actions, the term "opioid" was generally retained as a generic designation for all exogenous substances that bind stereo-specifically to any of several subspecies of opioid receptors and produce agonist actions.

The potential for the development of tolerance and physical dependence with repeated opioid use is a characteristic feature of all the opioid drugs, and the possibility of developing psychological dependence (i.e., addiction) is one of the major concerns in the use of the treatment of pain with opioids, even though iatrogenic addiction is rare. Another major concern associated with the use of opioids is the diversion of these drugs from the patient in pain to another (non-patient) for recreational purposes, e.g., to an addict.

The overall abuse potential of an opioid is not established by any one single factor. Instead, there is a composite of factors, including, the capacity of the drug to produce the kind of physical dependence in which drug withdrawal causes sufficient distress to bring about drug-seeking behavior; the ability to suppress withdrawal symptoms caused by withdrawal from other agents; the degree to which it induces euphoria similar to that produced by morphine and other opioids; the patterns of toxicity that occur when the drug is dosed above its normal therapeutic range; and physical characteristics of the drugs such as water solubility. Such physical characteristics may determine whether the drug is likely to be abused by the parenteral route.

In the United States, the effort to control the compulsive drug user includes efforts to control drug availability by placing restrictions on the use of opioids in the treatment of pain of compulsive drug users. In practice, the physician is often faced with a choice of administering potent opioid analgesics even to persons who seem predisposed to develop psychological dependence, i.e., addiction, on such drugs. In view of this problem, it has been recommended that these patients should not be given an opioid when another drug without a potential for abuse will suffice; and further that these patients should not be permitted to self-administer such drugs parenterally and should only be given a few days' supply at a time.

At least three basic patterns of opioid use and dependence have been identified. The first involves individuals whose drug use begins in the context of medical treatment and who obtain their initial supplies through, e.g., physicians. Another pattern begins with experimental or "recreational" drug use and progresses to more intensive use. A third pattern involves users who begin in one or another of the preceding ways but later switch to oral opioids such as methadone, obtained from organized addiction treatment programs.

Tolerance refers to the need to increase the dose of opioid over a period of time in order to achieve the same level of analgesia or euphoria, or the observation that repeated administration of the same dose results in decreased analgesia, euphoria, or other opioid effects. It has been found that a remarkable degree of tolerance develops to the respiratory depressant, analgesic, sedative, emetic and euphorigenic effects of opioids. However, the rate at which this tolerance may develop in either an addict or in a patient requiring treatment of pain, depends on the pattern of use. If the opioid is used frequently, it may be necessary to increase the dose. Tolerance does not develop equally or at the same rate to all the effects of opioids, and even users who are highly tolerant to respiratory depressant effects continue to exhibit miosis and constipation. Tolerance to opioids largely disappears when the withdrawal syndrome has been completed.

Physical dependence may develop upon repeated administrations or extended use of opioids. Physical dependence is gradually manifested after stopping opioid use or is precipitously manifested (e.g., within 20 minutes) after administration of a narcotic antagonist (referred to "precipitated withdrawal"). Depending upon the drug to which dependence has been established and the duration of use and dose, symptoms of withdrawal vary in number and kind, duration and severity. The most common symptoms of the withdrawal syndrome include anorexia, weight loss, pupillary dilation, chills alternating with excessive sweating, abdominal cramps, nausea, vomiting, muscle spasms, hyperirritability, lachrymation, rinorrhea, goose flesh and increased heart rate. Abstinence syndrome typically begins to occur 24–48 hours after the last dose, and the syndrome reaches its maximum intensity about the third day and may not begin to decrease until the third week.

Psychological dependence (i.e., addiction) on opioids is characterized by drug-seeking behavior directed toward achieving euphoria and escape from, e.g., psychosocioeconomic pressures. An addict will continue to administer opioids for non-medicinal purposes and in the face of self-harm.

Pharmacologically, opioid antagonists typically block or reverse all of the effect of opioid agonists. One use of opioid antagonists is as a once-a-day treatment of naltrexone to block euphoric effects that might be otherwise obtained upon administration of opioids to addicts. Small doses of opioid antagonists have been used to determine whether individuals are physically dependent on opioids. Most commonly, opioid antagonists are used to reverse the effects of opoids on individuals who have overdosed on opioid agonist drugs.

There have previously been attempts in the art to control the abuse potential associated with opioid analgesics. Typically, a particular dose of an opioid analgesic is more potent when administered parenterally as compared to the same dose administered orally. Therefore, one popular mode of abuse of oral medications involves the extraction of the opioid from the dosage form, and the subsequent injection of the opioid (using any "suitable" vehicle for injection) in order to achieve a "high." Attempts to curtail abuse have therefore typically centered around the inclusion in the oral dosage form of an opioid antagonist which is not orally active but which will substantially block the analgesic effects of the opioid if one attempts to dissolve the opioid and administer it parenterally.

For example, the combination of pentazocine and naloxone has been utilized in tablets available in the United States, commercially available as Talwin® Nx from Sanofi-Winthrop. Talwin® Nx contains pentazocine hydrochloride equivalent to 50 mg base and naloxone hydrochloride equivalent to 0.5 mg base. Talwin® Nx is indicated for the relief of moderate to severe pain. The amount of naloxone present in this combination has no action when taken orally, and will not interfere with the pharmacologic action of pentazocine. However, this amount of naloxone given by injection has profound antagonistic action to narcotic analgesics. Thus, the inclusion of naloxone is intended to curb a form of misuse of oral pentazocine which occurs when the dosage form is solubilized and injected. Therefore, this dosage has lower potential for parenteral misuse than previous oral pentazocine formulations. However, it is still subject to patient misuse and abuse by the oral route, for example, by the patient taking multiple doses at once.

Sunshine, et al. "Analgesic Efficacy of Pentazocine Versus a Pentazocine-Naloxone Combination Following Oral Administration", Clin. J. Pain, 1988:4:35–40, reported on the effect of the addition of 0.5 mg naloxone on the analgesic efficacy of pentazocine 50 mg. The combination was found to be significantly less efficacious than pentazocine for the sum of the pain intensity difference (SPID), and for relief and pain intensity difference (PID) at the fourth hour. For patients with moderate baseline pain, the combination produced significantly less pain relief than pentazocine for SPID and for relief and PID at hours 3 and 4. In patients with severe baseline pain, there was no significant difference found between pentazocine and the combination of pentazocine plus naloxone.

Wang, et al. "Crossover and Parallel Study of Oral Analgesics", J. Clin Pharmacol 1981; 21:162–8, studied the combination of naloxone 0.25 mg and Percodan® (composed of 4.5 mg oxycodone HCl, oxycodone terephthalate 0.28 mg, aspirin 224 mg, phenacetin 160 mg, and caffeine 32 mg) compared to Percodan® alone, and placebo in a crossover study of patients with chronic pain. The combination had lower mean scores than Percodan® alone for most of the analgesic hourly parameters in the later hours of the trial. However, for the summary variables, the combination showed no significant difference from either placebo or Percodan®.

A fixed combination of buprenorphine and naloxone was introduced in 1991 in New Zealand (Temgesic® Nx, Reckitt & Colman) for the treatment of pain.

A fixed combination therapy comprising tilidine (50 mg) and naloxone (4 mg) has been available in Germany for the management of severe pain since 1978 (Valoron® N, Goedecke). The rationale for the combination of these drugs is effective pain relief and the prevention of tilidine addiction through naloxone-induced antagonisms at the morphine receptor.

U.S. Pat. No. 3,773,955 (Pachter, et al.) described orally effective analgetic compositions which upon parenteral administration do not produce analgesia, euphoria, or physical dependence, and thereby prevent parenteral abuse of the analgetic agents. Such compositions contained from about 0.1 mg to about 10 mg naloxone per analgetic oral dose. This reference was not concerned with oral abuse of opioids.

U.S. Pat. No. 3,493,657 (Lewenstein, et al.) described compositions comprising naloxone and morphine or oxymorphone, which compositions were said to provide a strong analgesic effect without the occurrence of undesired side effects such as hallucinations.

U.S. Pat. No. 4,457,933 (Gordon, et al.) described a method for decreasing both the oral and parenteral abuse potential of strong analgetic agents such as oxycodone, propoxyphene and pentazocine, by combining an analgesic dose of the opioid with naloxone in a specific, relatively narrow range. Oxycodone-naloxone compositions having a ratio of 2.5–5:1 parts by weight and pentazocine-naloxone compositions having a ratio of 16–50:1 parts by weight were preferred. The dose of naloxone which was to be combined with the opioid is stated to substantially eliminate the possibility of either oral or parenteral abuse of the opioid without substantially affecting the oral analgesic activity thereof.

U.S. Pat. No. 4,582,835 (Lewis) describes a method of treating pain by administering a sublingually effective dose of buprenorphine with naloxone. Lewis describes dosage ratios of naloxone to buprenorphine from 1:3 to 1:1 for parenteral administration, and from 1:2 to 2:1 for sublingual administration.

It has been increasing recognized in the art that oral opioid formulations are not only being abused by the parenteral route, but also via the oral route when the patient or addict orally self-administers more than the prescribed oral dose during any dosage interval.

OBJECTS AND SUMMARY OF THE INVENTION

It is an object of the invention to provide an oral dosage form of an opioid analgesic which is subject to less abuse potential via the parenteral route of administration than prior commercially available dosage forms.

It is a further object of the invention to provide a method of treating pain in human patients with an oral dosage form of an opioid analgesic while reducing the parenteral abuse potential of dosage form.

It is a further object of the invention to provide a method of manufacturing an oral dosage form of an opioid analgesic such that it has less parenteral and/or oral abuse potential.

These objects and others are achieved by the present invention, which is directed in part to a method of reducing the abuse potential of an oral dosage form of an opioid analgesic, comprising combining an analgesically effective amount of an opioid agonist together with an opioid antagonist into an oral dosage form which would require at least a two-step extraction process to be separated from the opioid agonist, the amount of opioid antagonist including being sufficient to counteract opioid effects if extracted together with the opioid agonist and administered parenterally.

Preferably, the combination of the opioid agonist and the opioid antagonist are only extractable from the dosage form together, and thereafter must be separated from each other in a separate extraction step. For example, both the opioid agonist and the opioid antagonist may be soluble in acid, and must be separated utilizing a high pH solution. In one preferred embodiment, the opioid agonist is hydrocodone bitartrate and the opioid antagonist is naltrexone hydrochloride, wherein both the hydrocodone and naltrexone dissolve at a pH less than 8 and about 80% of said hydrocodone and about 10% of said naltrexone are extractable at a high pH, e.g., substantially greater than pH 10, and preferably above pH 11.

In other embodiments, the opioid agonist is hydromorphone hydrochloride and the opioid antagonist is naltrexone hydrochloride, or opioid agonist is oxycodone hydrochloride and the opioid antagonist is naltrexone hydrochloride; or the opioid agonist is morphine sulfate and the opioid antagonist is naltrexone hydrochloride.

In further embodiments, the method further comprises incorporating into the dosage form a further ingredient which makes separation of the opioid agonist from the opioid antagonist more difficult. Such further ingredients include gelling agents, waxes, or other pharmaceutically acceptable excipients.

In further embodiments, the method further comprises incorporating into the preparation of the dosage form one or more processing steps which further impede the separation of the opioid agonist from the opioid antagonist.

In certain preferred embodiments of the method, the opioid is hydrocodone, hydromorphone, oxycodone, morphine, or pharmaceutically acceptable salts thereof.

In certain preferred embodiments of the method, the opioid agonist and the opioid antagonist are combined in a ratio of opioid antagonist to opioid agonist (analgesic) which is analgesically effective when the combination is administered orally, but which is aversive in a physically dependent subject. In this manner, the combination product (antagonist/agonist) could in essence be therapeutic to one population (patients in pain), while being unacceptable (aversive) in a different population (e.g., physically dependent subjects) when orally administered at the same dose or at a higher dose than the usually prescribed dosage, e.g., about 2-3 times the usually prescribed dose of the opioid. Thus, the oral dosage form would have less potential for parenteral as well as oral abuse. In such embodiments where the opioid is hydrocodone and the antagonist is naltrexone, the ratio of naltrexone to hydrocodone is preferably from about 0.03–0.27:1 by weight, and more preferably from about 0.05–0.20:1 by weight. In such embodiments where the opioid antagonist is naltrexone and the opioid agonist is hydromorphone, the ratio of naltrexone to hydromorphone preferably is from about 0.148:1 to about 1.185:1, and more preferably from about 0.222:1 to about 0.889:1. In such embodiments where the opioid antagonist is naltrexone and the opioid agonist is morphine, the ratio of naltrexone to morphine is preferably from about 0.018:1 to about 0.148:1, and more preferably from about 0.028:1 to about 0.111:1. In such embodiments where the opioid antagonist is naltrexone and the opioid agonist is oxycodone, the ratio of naltrexone to oxycodone is preferably from about 0.037:1 to about 0.296:1, and more preferably from about 0.056:1 to about 0.222:1.

The dosage forms of the present invention may be liquids, tablets, or multiparticulate formulations, utilizing any desired pharmaceutically acceptable excipients known to those skilled in the art. However, it is preferred that the opioid agonist and opioid antagonist are incorporated into the oral dosage form in a manner which deters the easy separation of the two drugs.

In certain embodiments, the oral dosage forms of the present invention are sustained release formulations. This may be accomplished, e.g., via the incorporation of a sustained release carrier into a matrix containing the opioid agonist and opioid antagonist; or via a sustained release coating of a matrix containing the opioid agonist and opioid antagonist, where the sustained release coating contains at least a portion of the sustained release carrier included in the dosage form. In any event, it is preferred that the sustained release preparation be prepared in such a manner that the opioid agonist and the opioid antagonist are combined in a matrix or interdispersed so as to force an addict to utilize extraction methodology to separate these drugs.

The present invention is also directed to a method of treating pain in human patients in a manner which minimizes the likelihood of oral abuse of opioid analgesics, comprising administering to a human patient an oral dosage form the inventive combinations of opioid agonist/opioid antagonist which must be extracted in at least two separate extraction steps.

In certain embodiments, the opioid antagonist is included in an amount (i) which does not cause a reduction in the level of analgesia elicited from the dosage form upon oral administration to a non-therapeutic level and (ii) which provides at least a mildly negative, "aversive" experience in physically dependent subjects (e.g., precipitated abstinence syndrome) when the subjects attempt to take at least twice the usually prescribed dose at a time (and often 2–3 times that dose or more), as compared to a comparable dose of the opioid without the opioid antagonist present. In certain preferred embodiments, the amount of naltrexone included in the oral dosage form is less positively reinforcing (e.g., less "liked") to a non-physically dependent opioid addict than a comparable oral dosage form without the antagonist included. Preferably, the formulation provides effective analgesia when orally administered.

In certain preferred embodiments, the method further comprises incorporating the opioid agonist and opioid antagonist into a dosage form that includes a sustained release carrier, either included in the matrix or as a sustained release coating, such that the oral dosage form can be administered on a twice-a-day or a once-a-day basis.

The oral pharmaceutical compositions used in the methods of the present invention may be in the form of tablets, troches, lozenges, aqueous or oily suspensions, dispersable powders or granules, emulsions, hard or soft capsules or syrups or elixirs, microparticles (e.g., nicrocapsules, microspheres and the like), buccal tablets, etc.

The term "parenterally" as used herein includes subcutaneous injections, intravenous, intramuscular, intrasternal injection or infusion techniques.

The term "effective analgesia" is defined for purposes of the present invention as a satisfactory reduction in or elimination of pain, along with a tolerable level of side effects, as determined by the human patient. It is recognized that the ratio of opioid antagonist to opioid agonist included in certain embodiments of the invention (e.g., where the opioid antagonist is included in an amount (i) which does not cause a reduction in the level of analgesia elicited from the dosage form upon oral administration to a non-therapeutic level and (ii) which provides at least a mildly negative, "aversive" experience in physically dependent subjects when a large amount of the opioid, e.g., about 2–3 times the usually prescribed dose, is taken by or administered orally to a physically dependent subject) may decrease analgesia somewhat when the dosage form is orally administered as assessed by direct measurement in patients or by the use of one or more surrogate measures of opioid analgesic efficacy in human subjects such as a Visual Analogue Scale ("VAS") for "drug effect". The patient in pain may or may not appreciably notice the difference between the formulation administered in accordance with such embodiments of the invention, and a similar formulation which includes the same dose of opioid agonist without the opioid antagonist, but will obtain an analgesic effect from the combination. Surrogate measures of opioid efficacy (analgesia) include sedation, respiratory rate and/or pupil size (via pupillometry), and visual analogue scale ("VAS") for "drug effect". In such embodiments, such surrogate measures are affected in a direction which indicates reduced opioid effect, as compared to the same dose of opioid without the concommitant dose of opioid antagonist. The pharmacodynamic effect (analgesia) of the formulations administered in accordance with the invention can be described by means of, for example, scores from an analgesic questionnaire reported by the patients at serial times following administration of the dosage form. Summary measures of analgesia include the sum of pain intensity difference (SPID) and total pain relief (TOTPAR).

The term "sustained release" is defined for purposes of the present invention as the release of the drug (opioid analgesic) from the transdermal formulation at such a rate that blood (e.g., plasma) concentrations (levels) are maintained within the therapeutic range (above the minimum effective analgesic concentration or "MEAC") but below toxic levels over a period of time indicative of a twice-a-day or a once-a-day formulation.

For purposes of the present invention, the term "opioid agonist" is interchangeable with the term "opioid" or "opioid analgesic" and shall include the base of the opioid, pharmaceutically acceptable salts thereof, stereoisomers thereof, ethers and esters thereof, mixed agonist-antagonists, and partial agonists.

For purposes of the present invention, the term "opioid antagonist" shall include the base, pharmaceutically acceptable salts thereof, stereoisomers thereof, ethers and esters thereof, and mixtures thereof.

DETAILED DESCRIPTION OF THE INVENTION

It has been postulated that there exists at least three subspecies of opioid receptors, designated mu, kappa, and delta. Within this framework, the mu receptor is considered to be involved in the production of superspinal analgesia, respiratory depression, euphoria, and physical dependence. The kappa receptor is considered to be involved in inducing spinal analgesia, miosis and sedation. Activation of the gamma receptors causes dysphoria and hallucinations, as well as respiratory and vasomotor stimulatory effects. A receptor distinct from the mu receptor and designated gamma has been described in the mouse vas deferens, Lord, et al. *Nature*, 1977, 267, 495–99. Opioid agonists are thought to exert their agonist actions primarily at the mu receptor and to a lesser degree at the kappa receptor. There are a few drugs that appear to act as partial agonists at one receptor type or another. Such drugs exhibit a ceiling effect. Such drugs include nalorphine, propiram, and buprenorphine. Still other drugs act as competitive antagonists at the mu receptor and block the effects of morphine-like drugs, by exerting agonist actions at the kappa and omega receptors. The term "agonist-antagonist" has evolved to describe such mechanism of actions. The concept of antagonism to the actions of opioids is considered to be complex.

It has been found with the administration of opioid agonist-antagonists and partial agonists that tolerance develops to the agonist effects but not to the antagonist effects of the drugs. Even after prolonged administration of high doses, discontinuance of naloxone is not characterized by any recognizable withdrawal syndrome, and withdrawal of naltrexone, another relatively pure opioid antagonist, produces very few signs and symptoms. However, after prolonged administration of high dosage, abrupt discontinuation of opioid agonist-antagonists nalorphine or cyclazocine causes a characteristic withdrawal syndrome that is similar for both drugs.

Naloxone is an opioid antagonist which is almost void of agonist effects. Subcutaneous doses of up to 12 mg of naloxone produce no discernable subjective effects, and 24 mg naloxone causes only slight drowsiness. Small doses (0.4–0.8 mg) of naloxone given intramuscularly or intravenously in man prevent or promptly reverse the effects of morphine-like opioid agonist. One mg of naloxone intravenously has been reported to completely block the effect of 25 mg of heroin. The effects of naloxone are seen almost immediately after intravenous administration. The drug is absorbed after oral administration, but has been reported to be metabolized into an inactive form rapidly in its first passage through the liver such that it has been reported to be only one fiftieth as potent as when parenterally administered. Oral dosage of more than 1g have been reported to be almost completely metabolized in less than 24 hours.

Other opioid antagonists, for example, cyclazocine and naltrexone, both of which have cyclopropylmethyl substitutions on the nitrogen, retain much of their efficacy by the oral route and their durations of action are much longer, approaching 24 hours after oral doses. A most preferred opioid antagonist is naltrexone. However, equiantagonistic oral doses of other opioid antagonists, including but not limited to naloxone, nalmephene, cyclazocine, and levallorphan can be utilized in accordance with the present invention. The ratio of such other antagonists to a particular opioid agonist can be readily determined without undue experimentation by one skilled in art who desires to utilize a different opioid antagonist than naltrexone, the ratio of which to opioid agonists is exemplified and discussed in detail herein. Those skilled in the art may determine such ratios of other antagonists to opioid agonists, e.g., by conducting the same or similar clinical studies set forth in the examples appended herein. Thus, combinations of opioid antagonists/opioid agonists which are orally administered in ratios which are equivalent to the ratio of, e.g., naltrexone to hydrocodone set forth herein are considered to be within the scope of the present invention and within the scope of the appended claims. For example, in certain embodiments of the invention, naloxone is utilized as the opioid antagonist, the amount of naloxone included in the dosage form being large enough to provide an equiantagonistic effect as if naltrexone were included in the combination.

In the treatment of patients previously addicted to opioids, naltrexone has been used in large oral doses (over 100 mg) to prevent euphorigenic effects of opioid agonists. Naltrexone has been reported to exert strong preferential blocking action against mu over delta sites. Naltrexone is known as a synthetic congener of oxymorphone with no opioid agonist properties, and differs in structure from oxymorphone by the replacement of the methyl group located on the nitrogen atom of oxymorphone with a cyclopropylmethyl group. The hydrochloride salt of naltrexone is soluble in water up to about 100 mg/cc. The pharmacological and pharmacokinetic properties of naltrexone have been evaluated in multiple animal and clinical studies. See, e.g., Gonzalez J P, et al. Naltrexone: A review of its Pharmacodynamic and Pharmacokinetic Properties and Therapeutic Efficacy in the Management of Opioid Dependence. Drugs 1988; 35:192–213, hereby incorporated by reference. Following oral administration, naltrexone is rapidly absorbed (within 1 hour) and has an oral bioavailability ranging from 5–40%. Naltrexone's protein binding is approximately 21% and the volume of distribution following single-dose administration is 16.1 L/kg.

Naltrexone is commercially available in tablet form (Revia®, DuPont) for the treatment of alcohol dependence and for the blockade of exogenously administered opioids. See, e.g., Revia (naltrexone hydrochloride tablets). *Physician's Desk Reference* 51$^{st}$ ed., Montvale, N.J. Medical Economics 1997; 51:957–959. A dosage of 50 mg ReVia® blocks the pharmacological effects of 25 mg IV administered heroin for up to 24 hours.

It is known that when coadministered with morphine, heroin or other opioids on a chronic basis, naltrexone blocks the development of physical dependence to opioids. It is believed that the method by which naltrexone blocks the effects of heroin is by competitively binding at the opioid receptors. Naltrexone has been used to treat narcotic addiction by complete blockade of the effects of opioids. It has been found that the most successful use of naltrexone for a narcotic addiction is with good prognosis narcotic addicts as part of a comprehensive occupational or rehabilitative program involving behavioral control or other compliance enhancing methods. For treatment of narcotic dependence with naltrexone, it is desirable that the patient be opioid-free for at least 7–10 days. The initial dosage of naltrexone for such purposes has typically been about 25 mg, and if no withdrawal signs occur, the dosage may be increased to 50 mg per day. A daily dosage of 50 mg is considered to produce adequate clinical blockade of the actions of parenterally administered opioids. Naltrexone has also been used for the treatment of alcoholism as an adjunct with social and psychotherapeutic methods.

In the dosage forms and methods of the invention, the amount of naltrexone included is significantly less than the dosages previously commercially available. This is in part because the use of naltrexone is different in the present invention: the goal is not to block opioid effects, but rather to provide a negative, "aversive" experience when a large amount of the combination product, e.g., about 2–3 times the usually prescribed dose, is taken by or administered to a physically dependent subject.

Thus, for example, in formulations of the present invention in which the opioid is hydrocodone bitartrate 15 mg, the amount of naltrexone hydrochloride included in the formulation is from about 0.5 mg to about 4 mg, and preferably from about 0.75 mg to about 3 mg naltrexone per 15 mg hydrocodone.

Opioid analgesics which are useful in the present invention include all opioid agonists or mixed agonist-antagonists, partial agonists, including but not limited to alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tilidine, tramadol, mixtures of any of the foregoing, salts of any of the foregoing, and the like.

In certain preferred embodiments, the opioid agonist or analgesic is selected from the group consisting of hydrocodone, morphine, hydromorphone, oxycodone, codeine, levorphanol, meperidine, methadone, or salts thereof, or mixtures thereof. In certain preferred embodiments, the opioid agonist is hydrocodone. Equianalgesic doses of these opioids, in comparision to a 15 mg dose of hydrocodone, are set forth in Table 1 below:

TABLE 1

Equianalgesic Doses of Opioids

| Opioid | Calculated Dose (mg) |
|---|---|
| Oxycodone | 13.5 |
| Codeine | 90.0 |
| Hydrocodone | 15.0 |
| Hydromorphone | 3.375 |
| Levorphanol | 1.8 |
| Meperidine | 135.0 |
| Methadone | 9.0 |
| Morphine | 27.0 |

Based on the preferred ratio of naltrexone in an amount from about 0.5 to about 4 mg per 15 mg of hydrocodone, the approximate ratio of naltrexone to 1 mg of each opioid is set forth in Table 2:

TABLE 2

Weight Ratio of Naltrexone per Dose Opioid

| Opioid | Weight Ratio Naltrexone per 1 mg Opioid |
|---|---|
| Oxycodone | 0.037 to 0.296 |
| Codeine | 0.005 to 0.044 |
| Hydrocodone | 0.033 to 0.267 |
| Hydromorphone | 0.148 to 1.185 |
| Levorphanol | 0.278 to 2.222 |
| Meperidine | 0.0037 to 0.0296 |
| Methadone | 0.056 to 0.444 |
| Morphine | 0.018 to 0.148 |

Based on the more preferred ratio of about 0.75 mg to about 3 mg naltrexone per 15 mg hydrocodone of naltrexone, the approximate ratio of naltrexone to 1 mg of each opioid is set forth in Table 3:

TABLE 3

Weight Ratio of Naltrexone per Dose Opioid

| Opioid | Weight Ratio Naltrexone |
|---|---|
| Oxycodone | 0.056 to 0.222 |
| Codeine | 0.0083 to 0.033 |
| Hydrocodone | 0.050 to 0.200 |
| Hydromorphone | 0.222 to 0.889 |
| Levorphanol | 0.417 to 1.667 |
| Meperidine | 0.0056 to 0.022 |
| Methadone | 0.083 to 0.333 |
| Morphine | 0.028 to 0.111 |

Although hydrocodone is effective in the management of pain, there has been an increase in its abuse by individuals who are psychologically dependent on opioids or who misuse opioids for non-therapeutic reasons. Previous experience with other opioids has demonstrated a decreased abuse potential when opioids are administered in combination with a narcotic antagonist especially in patients who are ex-addicts. Weinhold L L, et al. Buprenorphine Alone and in Combination with Naltrexone in Non-Dependent Humans, *Drug and Alcohol Dependence* 1992; 30:263–274; Mendelson J., et. al., Buprenorphine and Naloxone Interactions in Opiate-Dependent Volunteers, *Clin Pharm Ther* 1996; 60:105–114; both of which are hereby incorporated by reference.

Hydrocodone is a semisynthetic narcotic analgesic and antitussive with multiple central nervous system and gastrointestinal actions. Chemically, hydrocodone is 4,5-epoxy-3-methoxy-17-methylmorphinan-6-one, and is also known as dihydrocodeinone. Like other opioids, hydrocodone may be habit forming and may produce drug dependence of the morphine type. In excess doses hydrocodone, like other opium derivatives, will depress respiration.

Oral hydrocodone is also available in Europe (Belgium, Germany, Greece, Italy, Luxembourg, Norway and Switzerland) as an antitussive agent. A parenteral formulation is also available in Germany as an antitussive agent. For use as an analgesic, hydrocodone bitartrate is commercially available in the United States only as a fixed combination with non-opiate drugs (i.e., ibuprofen, acetaminophen, aspirin, etc.) for relief of moderate or moderately severe pain.

A common dosage form of hydrocodone is in combination with acetaminophen, and is commercially available, e.g., as Lortab® in the U.S. from UCB Pharma, Inc. as 2.5/500 mg, 5/500 mg, 7.5/500 mg and 10/500 mg hydrocodone/acetaminophen tablets. Tablets are also available in the ratio of 7.5 mg hydrocodone bitartrate and 650 mg acetaminophen; and 7.5 mg hydrocodone bitartrate and 750 mg acetaminophen. Hydrocodone in combination with aspirin is given in an oral dosage form to adults generally in 1–2 tablets every 4–6 hours as needed to alleviate pain. The tablet form is 5 mg hydrocodone bitartrate and 224 mg aspirin with 32 mg caffeine; or 5 mg hydrocodone bitartrate and 500 mg aspirin. A relatively new formulation comprises hydrocodone bitartrate and ibuprofen. Vicoprofen®, commercially available in the U.S. from Knoll Laboratories, is a tablet containing 7.5 mg hydrocodone bitartrate and 200 mg ibuprofen. The present invention is contemplated to encompass all such formulations, with the inclusion of the orally active opioid antagonist within the inventive amounts set forth herein.

The abuse potential of opioid analgesics such as hydrocodone is surprisingly curtailed by the inventive combinations of the present invention. More particularly, it has been discovered that it is possible to combine in a single oral dosage form an opioid analgesic together with a small amount of opioid antagonist, to achieve a product which still provides analgesia but which substantially negates the possibility that a physically dependent human subject will continue to abuse the drug by taking more than one tablet at a time, e.g., 2–3 times more than the usually prescribed dose.

The oral dosage forms of the invention comprise an orally therapeutically effective amount of an opioid agonist, together with an opioid antagonist such as naltrexone in an amount (i) which does not cause a reduction in the level of analgesia elicited from the dosage form upon oral administration to a non-therapeutic level and (ii) which provides at least a mildly negative, "aversive" experience in physically dependent human subjects, for example, physically dependent addicts (e.g., precipitated abstinence syndrome) when taking more than the usually prescribed dose at a time. Preferably, the amount of antagonist included in the oral dosage form is (iii) less positively reinforcing (e.g., less "liked") by a non-physically dependent human subject, e.g., opioid addict, than a comparable oral dosage form without the antagonist included.

The amount of antagonist which is useful to achieve parameters (i)–(iii) set forth in the preceding paragraph may be determined at least in part, for example, through the use of "surrogate" tests, such as a VAS scale (where the subject grades his/her perception of the effect of the dosage form) and/or via a measurement such as pupil size (measured by pupillometry). Such measurements allow one skilled in the art to determine the dose of antagonist relative to the dose of agonist which causes a diminution in the opiate effects of the agonist. Subsequently, one skilled in the art can determine the level of opioid antagonist that causes aversive effects in physically dependent subjects as well as the level of opioid antagonist that minimizes "liking scores" or opioid reinforcing properties in non-physically dependent addicts. Once these levels of opioid antagonist are determined, it is then possible to determine the range of antagonist dosages at or below this level which would be useful in achieving parameters (i)–(iii) set forth in the preceding paragraph.

The combination of opioid agonist and opioid antagonist can be employed in admixtures with conventional excipients, i.e., pharmaceutically acceptable organic or inorganic carrier substances suitable for oral administration, known to the art. Suitable pharmaceutically acceptable carriers include but are not limited to water, salt solutions, alcohols, gum arabic, vegetable oils, benzyl alcohols, polyethylene glycols, gelate, carbohydrates such as lactose, amylose or starch, magnesium stearate talc, silicic acid, viscous paraffin, perfume oil, fatty acid monoglycerides and diglycerides, pentaerythritol fatty acid esters, hydroxymethylcellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They can also be combined where desired with other active agents, e.g., other analgesic agents. For oral administration, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients which are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay release of the active ingredients. Formulations for oral use may also be presented as hard gelatin capsules wherein the active ingredient is mixed with an inert diluent.

Aqueous suspensions contain the above-identified combination of drugs and that mixture has one or more excipients suitable as suspending agents, for example pharmaceutically acceptable synthetic gums such as hydroxypropylmethylcellulose or natural gums. Oily suspensions may be formulated by suspending the above-identified combination of drugs in a vegetable oil or mineral oil. The oily suspensions may contain a thickening agent such as beeswax or cetyl alcohol. A syrup, elixir, or the like can be used wherein a sweetened vehicle is employed. Injectable suspensions may also be prepared, in which case appropriate liquid carriers, suspending agents and the like may be employed.

The method of treatment and pharmaceutical formulations of the present invention may further include one or more drugs in addition to the opioid analgesic and opioid antagonist, which additional drug(s) may or may not act synergistically therewith. Thus, in certain embodiments, a combination of two opioid analgesics may be included in the formulation, in addition to the opioid antagonist. For example, the dosage form may include two opioid analgesics having different properties, such as half-life, solubility, potency, and a combination of any of the foregoing. In yet further embodiments, one or more opioid analgesics is included and a further non-opioid drug is also included, in addition to the opioid antagonist. Such non-opioid drugs would preferably provide additional analgesia, and include, for example, aspirin; acetaminophen; non-sterioidal antiinflammatory drugs ("NSAIDS"), e.g., ibuprofen, ketoprofen, etc.; N-methyl-D-aspartate (NMDA) receptor antagonists, e.g., a morphinan such as dextromethorphan or dextrorphan, or ketamine; cycooxygenase-II inhibitors ("COX-II inhibitors"); and/or glycine receptor antagonists.

In certain preferred embodiments of the present invention, the invention allows for the use of lower doses of the opioid analgesic by virtue of the inclusion of an additional non-opioid agonist, such as an NSAID or a COX-2 inhibitor. By using lower amounts of either or both drugs, the side effects associated with effective pain management in humans are reduced.

Suitable non-steroidal anti-inflammatory agents, including ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zido-metacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam or isoxicam, and the like. Useful dosages of these drugs are well known to those skilled in the art.

N-methyl-D-aspartate (NMDA) receptor antagonists are well known in the art, and encompass, for example, morphinans such as dextromethorphan or dextrorphan, ketamine, d-methadone or pharmaceutically acceptable salts thereof. For purposes of the present invention, the term "NMDA antagonist" is also deemed to encompass drugs that block a major intracellular consequence of NMDA-receptor activation, e.g. a ganglioside such as $GM_1$ or $GT_{1b}$, a phenothiazine such as trifluoperazine or a naphthalenesulfonamide such as N-(6-aminothexyl)-5-chloro-1-naphthalenesulfonamide. These drugs are stated to inhibit the development of tolerance to and/or dependence on addictive drugs, e.g., narcotic analgesics such as morphine, codeine, etc. in U.S. Pat. Nos. 5,321,012 and 5,556,838 (both to Mayer, et. al.), and to treat chronic pain in U.S. Pat. No. 5,502,058 (Mayer, et.al.), all of which are hereby incorporated by reference. The NMDA antagonist may be included alone, or in combination with a local anesthetic such as lidocaine, as described in these Mayer, et.al. patents.

The treatment of chronic pain via the use of glycine receptor antagonists and the identification of such drugs is described in U.S. Pat. No. 5,514,680 (Weber, et al.), hereby incorporated by reference.

COX-2 inhibitors have been reported in the art and many chemical structures are known to produce inhibition of cyclooxygenase-2. COX-2 inhibitors are described, for example, in U.S. Pat. Nos. 5,616,601; 5,604,260; 5,593,994; 5,550,142; 5,536,752; 5,521,213; 5,475,995; 5,639,780; 5,604,253; 5,552,422; 5,510,368; 5,436,265; 5,409,944; and 5,130,311, all of which are hereby incorporated by reference. Certain preferred COX-2 inhibitors include celecoxib (SC-58635), DUP-697, flosulide (CGP-28238), meloxicam, 6-methoxy-2 naphthylacetic acid (6-MNA), MK-966, nabumetone (prodrug for 6-MNA), nimesulide, NS-398, SC-5766, SC-58215, T-614; or combinations thereof. Dosage levels of COX-2 inhibitor on the order of from about 0.005 mg to about 140 mg per kilogram of body weight per day are therapeutically effective in combination with an opioid analgesic. Alternatively, about 0.25 mg to about 7 g per patient per day of a COX-2 inhibitor is administered in combination with an opioid analgesic.

In yet further embodiments, a non-opioid drug can be included which provides a desired effect other than analgesia, e.g., antitussive, expectorant, decongestant, antihistamine drugs, local anesthetics, and the like.

An oral dosage form according to the invention may be provided as, for example, granules, spheroids, beads, pellets (hereinafter collectively referred to as "multiparticulates"). An amount of the multiparticulates which is effective to provide the desired dose of opioid over time may be placed in a capsule or may be incorporated in any other suitable oral solid form. Alternatively, the oral dosage form may be in the form of a tablet.

Controlled Release Dosage Forms

The opioid agonist/opioid antagonist combination can be formulated as a controlled or sustained release oral formulation in any suitable tablet, coated tablet or multiparticulate formulation known to those skilled in the art. The sustained release dosage form may optionally include a sustained release carrier which is incorporated into a matrix along with the opioid agonist and opioid antagonist, or may be applied as a sustained release coating.

In embodiments in which the opioid analgesic comprises hydrocodone, the sustained release oral dosage forms may include analgesic doses from about 8 mg to about 50 mg of hydrocodone per dosage unit. In sustained release oral dosage forms where hydromorphone is the therapeutically active opioid, it is included in an amount from about 2 mg to about 64 mg hydromorphone hydrochloride. In another embodiment, the opioid analgesic comprises morphine, and the sustained release oral dosage forms of the present invention include from about 2.5 mg to about 800 mg morphine, by weight. In yet another embodiment, the opioid analgesic comprises oxycodone and the sustained release oral dosage forms include from about 2.5 mg to about 800 mg oxycodone. The opioid analgesic may comprise tramadol and the sustained release oral dosage forms may include from about 25 mg to 800 mg tramadol per dosage unit. The dosage form may contain more than one opioid analgesic to provide a substantially equivalent therapeutic effect. Alternatively, the dosage form may contain molar equivalent amounts of other salts of the opioids useful in the present invention.

In one preferred embodiment of the present invention, the sustained release dosage form comprises such particles containing or comprising the active ingredient, wherein the particles have diameter from about 0.1 mm to about 2.5 mm, preferably from about 0.5 mm to about 2 mm.

The particles are preferably film coated with a material that permits release of the opioid agonist/antagonist combination at a sustained rate in an aqueous medium. The film coat is chosen so as to achieve, in combination with the other stated properties, a desired in-vitro release rate. The sustained release coating formulations of the present invention should be capable of producing a strong, continuous film that is smooth and elegant, capable of supporting pigments and other coating additives, non-toxic, inert, and tack-free.

In certain embodiments, the particles comprise normal release matrixes containing the opioid analgesic with the opioid antagonist.

Coatings

The dosage forms of the present invention may optionally be coated with one or more materials suitable for the regulation of release or for the protection of the formulation. In one embodiment, coatings are provided to permit either pH-dependent or pH-independent release, e.g., when exposed to gastrointestinal fluid. A pH-dependent coating serves to release the opioid in desired areas of the gastro-intestinal (GI) tract, e.g., the stomach or small intestine, such that an absorption profile is provided which is capable of providing at least about eight hours and preferably about twelve hours to up to about twenty-four hours of analgesia to a patient. When a pH-independent coating is desired, the coating is designed to achieve optimal release regardless of pH-changes in the environmental fluid, e.g., the GI tract. It is also possible to formulate compositions which release a portion of the dose in one desired area of the GI tract, e.g., the stomach, and release the remainder of the dose in another area of the GI tract, e.g., the small intestine.

Formulations according to the invention that utilize pH-dependent coatings to obtain formulations may also impart a repeat-action effect whereby unprotected drug is coated over the enteric coat and is released in the stomach, while the remainder, being protected by the enteric coating, is released further down the gastrointestinal tract. Coatings which are pH-dependent may be used in accordance with the present invention include shellac, cellulose acetate phthalate (CAP), polyvinyl acetate phthalate (PVAP), hydroxypropylmethylcellulose phthalate, and methacrylic acid ester copolymers, zein, and the like.

In certain preferred embodiments, the substrate (e.g., tablet core bead, matrix particle) containing the opioid analgesic (with or without the COX-2 inhibitor) is coated with a hydrophobic material selected from (i) an alkylcellulose; (ii) an acrylic polymer; or (iii) mixtures thereof. The coating may be applied in the form of an organic or aqueous solution or dispersion. The coating may be applied to obtain a weight gain from about 2 to about 25% of the substrate in order to obtain a desired sustained release profile. Coatings derived from aqueous dispersions are described, e.g., in detail in U.S. Pat. Nos. 5,273,760 and 5,286,493, assigned to the Assignee of the present invention and hereby incorporated by reference.

Other examples of sustained release formulations and coatings which may be used in accordance with the present invention include Assignee's U.S. Pat. Nos. 5,324,351; 5,356,467, and 5,472,712, hereby incorporated by reference in their entirety.

Alkylcellulose Polymers

Cellulosic materials and polymers, including alkylcelluloses, provide hydrophobic materials well suited for coating the beads according to the invention. Simply by way of example, one preferred alkylcellulosic polymer is ethylcellulose, although the artisan will appreciate that other cellulose and/or alkylcellulose polymers may be readily employed, singly or in any combination, as all or part of a hydrophobic coating according to the invention.

One commercially-available aqueous dispersion of ethylcellulose is Aquacoat® (FMC Corp., Philadelphia, Pa., U.S.A.). Aquacoat® is prepared by dissolving the ethylcellulose in a water-immiscible organic solvent and then emulsifying the same in water in the presence of a surfactant and a stabilizer. After homogenization to generate submicron droplets, the organic solvent is evaporated under vacuum to form a pseudolatex. The plasticizer is not incorporated in the pseudolatex during the manufacturing phase. Thus, prior to using the same as a coating, it is necessary to intimately mix the Aquacoat® with a suitable plasticizer prior to use.

Another aqueous dispersion of ethylcellulose is commercially available as Surelease® (Colorcon, Inc., West Point, Pa., U.S.A.). This product is prepared by incorporating plasticizer into the dispersion during the manufacturing process. A hot melt of a polymer, plasticizer (dibutyl sebacate), and stabilizer (oleic acid) is prepared as a homogeneous mixture, which is then diluted with an alkaline solution to obtain an aqueous dispersion which can be applied directly onto substrates.

Acrylic Polymers

In other preferred embodiments of the present invention, the hydrophobic material comprising the controlled release coating is a pharmaceutically acceptable acrylic polymer, including but not limited to acrylic acid and methacrylic acid copolymers, methyl methacrylate copolymers, ethoxyethyl methacrylates, cyanoethyl methacrylate, poly(acrylic acid), poly(methacrylic acid), methacrylic acid alkylamide copolymer, poly(methyl methacrylate), polymethacrylate, poly(methyl methacrylate) copolymer, polyacrylamide, aminoalkyl methacrylate copolymer, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In order to obtain a desirable dissolution profile, it may be necessary to incorporate two or more ammonio methacrylate copolymers having differing physical properties, such as different molar ratios of the quaternary ammonium groups to the neutral (meth)acrylic esters.

Certain methacrylic acid ester-type polymers are useful for preparing pH-dependent coatings which may be used in accordance with the present invention. For example, there are a family of copolymers synthesized from diethylaminoethyl methacrylate and other neutral methacrylic esters, also known as methacrylic acid copolymer or polymeric methacrylates, commercially available as Eudragit® from R öhm Tech, Inc. There are several different types of Eudragit®. For example, Eudragit® E is an example of a methacrylic acid copolymer which swells and dissolves in acidic media. Eudragit® L is a methacrylic acid copolymer which does not swell at about pH<5.7 and is soluble at about pH>6. Eudragit® S does not swell at about pH<6.5 and is soluble at about pH>7. Eudragit® RL and Eudragit® RS are water swellable, and the amount of water absorbed by these polymers is pH-dependent, however, dosage forms coated with Eudragit® RL and RS are pH-independent.

In certain preferred embodiments, the acrylic coating comprises a mixture of two acrylic resin lacquers commercially available from Rohm Pharma under the Tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. The code designations RL (high permeability) and RS (low permeability) refer to the permeability properties of these agents. Eudragit® RL/RS mixtures are insoluble in water and in digestive fluids. However, coatings formed from the same are swellable and permeable in aqueous solutions and digestive fluids.

The Eudragit® RL/RS dispersions of the present invention may be mixed together in any desired ratio in order to ultimately obtain a sustained release formulation having a desirable dissolution profile. Desirable sustained release formulations may be obtained, for instance, from a retardant coating derived from 100% Eudragit® RL, 50% Eudragit® RL and 50% Eudragit® RS, and 10% Eudragit® RL:Eudragit® 90% RS. Of course, one skilled in the art will recognize that other acrylic polymers may also be used, such as, for example, Eudragit® L.

Plasticizers

In embodiments of the present invention where the coating comprises an aqueous dispersion of a hydrophobic material, the inclusion of an effective amount of a plasticizer in the aqueous dispersion of hydrophobic material will further improve the physical properties of the sustained release coating. For example, because ethylcellulose has a relatively high glass transition temperature and does not form flexible films under normal coating conditions, it is preferable to incorporate a plasticizer into an ethylcellulose coating containing sustained release coating before using the same as a coating material. Generally, the amount of plasticizer included in a coating solution is based on the concentration of the film-former, e.g., most often from about 1 to about 50 percent by weight of the film-former. Concentration of the plasticizer, however, can only be properly determined after careful experimentation with the particular coating solution and method of application.

Examples of suitable plasticizers for ethylcellulose include water insoluble plasticizers such as dibutyl sebacate, diethyl phthalate, triethyl citrate, tributyl citrate, and triacetin, although it is possible that other water-insoluble plasticizers (such as acetylated monoglycerides, phthalate esters, castor oil, etc.) may be used. Triethyl citrate is an especially preferred plasticizer for the aqueous dispersions of ethyl cellulose of the present invention.

Examples of suitable plasticizers for the acrylic polymers of the present invention include, but are not limited to citric acid esters such as triethyl citrate NF XVI, tributyl citrate, dibutyl phthalate, and possibly 1,2-propylene glycol. Other plasticizers which have proved to be suitable for enhancing the elasticity of the films formed from acrylic films such as Eudragit® RL/RS lacquer solutions include polyethylene glycols, propylene glycol, diethyl phthalate, castor oil, and triacetin. Triethyl citrate is an especially preferred plasticizer for the aqueous dispersions of ethyl cellulose of the present invention.

It has further been found that the addition of a small amount of talc reduces the tendency of the aqueous dispersion to stick during processing, and acts as a polishing agent.

Processes for Preparing Coated Beads

When a hydrophobic material is used to coat inert pharmaceutical beads such as nu pariel 18/20 beads, a plurality of the resultant solid controlled release beads may thereafter be placed in a gelatin capsule in an amount sufficient to provide an effective controlled release dose when ingested and contacted by an environmental fluid, e.g., gastric fluid or dissolution media.

The controlled release bead formulations of the present invention slowly release the therapeutically active agent, e.g., when ingested and exposed to gastric fluids, and then to intestinal fluids. The controlled release profile of the formulations of the invention can be altered, for example, by varying the amount of overcoating with the hydrophobic material, altering the manner in which the plasticizer is added to the hydrophobic material, by varying the amount of plasticizer relative to hydrophobic material, by the inclusion of additional ingredients or excipients, by altering the method of manufacture, etc. The dissolution profile of the ultimate product may also be modified, for example, by increasing or decreasing the thickness of the retardant coating.

Spheroids or beads coated with a therapeutically active agent are prepared, e.g., by dissolving the therapeutically active agent in water and then spraying the solution onto a substrate, for example, nu pariel 18/20 beads, using a Wuster insert. Optionally, additional ingredients are also added prior to coating the beads in order to assist the binding of the opioid to the beads, and/or to color the solution, etc. For example, a product which includes hydroxypropylmethylcellulose, etc. with or without colorant (e.g., Opadry®, commercially available from Colorcon, Inc.) may be added to the solution and the solution mixed (e.g., for about 1 hour) prior to application of the same onto the beads. The resultant coated substrate, in this example beads, may then be optionally overcoated with a barrier agent, to separate the therapeutically active agent from the hydrophobic controlled release coating. An example of a suitable barrier agent is one which comprises hydroxypropylmethylcellulose. However, any film-former known in the art may be used. It is preferred that the barrier agent does not affect the dissolution rate of the final product.

The beads may then be overcoated with an aqueous dispersion of the hydrophobic material. The aqueous dispersion of hydrophobic material preferably further includes an effective amount of plasticizer, e.g. triethyl citrate. Preformulated aqueous dispersions of ethyl-cellulose, such as Aquacoat® or Surelease®, may be used. If Surelease® is used, it is not necessary to separately add a plasticizer. Alternatively, pre-formulated aqueous dispersions of acrylic polymers such as Eudragit® can be used.

The coating solutions of the present invention preferably contain, in addition to the film-former, plasticizer, and solvent system (i.e., water), a colorant to provide elegance and product distinction. Color may be added to the solution of the therapeutically active agent instead, or in addition to the aqueous dispersion of hydrophobic material. For example, color may be added to Aquacoat® via the use of alcohol or propylene glycol based color dispersions, milled aluminum lakes and opacifiers such as titanium dioxide by adding color with shear to water soluble polymer solution and then using low shear to the plasticized Aquacoat®. Alternatively, any suitable method of providing color to the formulations of the present invention may be used. Suitable ingredients for providing color to the formulation when an aqueous dispersion of an acrylic polymer is used include titanium dioxide and color pigments, such as iron oxide pigments. The incorporation of pigments, may, however, increase the retard effect of the coating.

Plasticized hydrophobic material may be applied onto the substrate comprising the therapeutically active agent by spraying using any suitable spray equipment known in the art. In a preferred method, a Wurster fluidized-bed system is used in which an air jet, injected from underneath, fluidizes the core material and effects drying while the acrylic polymer coating is sprayed on. A sufficient amount of the hydrophobic material to obtain a predetermined controlled release of said therapeutically active agent when the coated substrate is exposed to aqueous solutions, e.g. gastric fluid, is preferably applied, taking into account the physical characteristics of the therapeutically active agent, the manner of incorporation of the plasticizer, etc. After coating with the hydrophobic material, a further overcoat of a film-former, such as Opadry®, is optionally applied to the beads. This overcoat is provided, if at all, in order to substantially reduce agglomeration of the beads.

The release of the therapeutically active agent from the controlled release formulation of the present invention can be further influenced, i.e., adjusted to a desired rate, by the addition of one or more release-modifying agents, or by providing one or more passageways through the coating. The ratio of hydrophobic material to water soluble material is determined by, among other factors, the release rate required and the solubility characteristics of the materials selected.

The release-modifying agents which function as pore-formers may be organic or inorganic, and include materials that can be dissolved, extracted or leached from the coating in the environment of use. The pore-formers may comprise one or more hydrophilic materials such as hydroxypropylmethylcellulose.

The sustained release coatings of the present invention can also include erosion-promoting agents such as starch and gums.

The sustained release coatings of the present invention can also include materials useful for making microporous lamina in the environment of use, such as polycarbonates comprised of linear polyesters of carbonic acid in which carbonate groups reoccur in the polymer chain.

The release-modifying agent may also comprise a semipermeable polymer.

In certain preferred embodiments, the release-modifying agent is selected from hydroxypropylmethylcellulose, lactose, metal stearates, and mixtures of any of the foregoing.

The sustained release coatings of the present invention may also include an exit means comprising at least one passageway, orifice, or the like. The passageway may be formed by such methods as those disclosed in U.S. Pat. Nos. 3,845,770; 3,916,889; 4,063,064; and 4,088,864 (all of which are hereby incorporated by reference). The passageway can have any shape such as round, triangular, square, elliptical, irregular, etc.

Matrix Bead Formulations

In other embodiments of the present invention, the controlled release formulation is achieved via a matrix having a controlled release coating as set forth above. The present invention may also utilize a controlled release matrix that affords in-vitro dissolution rates of the opioid within the preferred ranges and that releases the opioid in a pH-dependent or pH-independent manner. The materials suitable for inclusion in a controlled release matrix will depend on the method used to form the matrix.

For example, a matrix in addition to the opioid analgesic and (optionally) COX-2 may include:

Hydrophilic and/or hydrophobic materials, such as gums, cellulose ethers, acrylic resins, protein derived materials; the list is not meant to be exclusive, and any pharmaceutically acceptable hydrophobic material or hydrophilic material which is capable of imparting controlled release of the active agent and which melts (or softens to the extent necessary to be extruded) may be used in accordance with the present invention.

Digestible, long chain ($C_8$–$C_{50}$, especially $C_{12}$–$C_{40}$), substituted or unsubstituted hydrocarbons, such as fatty acids, fatty alcohols, glyceryl esters of fatty acids, mineral and vegetable oils and waxes, and stearyl alcohol; and polyalkylene glycols.

Of these polymers, acrylic polymers, especially Eudragit® RSPO—the cellulose ethers, especially hydroxyalkylcelluloses and carboxyalkylcelluloses, are preferred. The oral dosage form may contain between 1% and 80% (by weight) of at least one hydrophilic or hydrophobic material.

When the hydrophobic material is a hydrocarbon, the hydrocarbon preferably has a melting point of between 25° and 90° C. Of the long chain hydrocarbon materials, fatty (aliphatic) alcohols are preferred. The oral dosage form may contain up to 60% (by weight) of at least one digestible, long chain hydrocarbon.

Preferably, the oral dosage form contains up to 60% (by weight) of at least one polyalkylene glycol.

The hydrophobic material is preferably selected from the group consisting of alkylcelluloses, acrylic and methacrylic acid polymers and copolymers, shellac, zein, hydrogenated castor oil, hydrogenated vegetable oil, or mixtures thereof. In certain preferred embodiments of the present invention, the hydrophobic material is a pharmaceutically acceptable acrylic polymer, including but not limited to acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer, poly(methyl methacrylate), poly (methacrylic acid)(anhydride), polymethacrylate, polyacrylamide, poly(methacrylic acid anhydride), and glycidyl methacrylate copolymers. In other embodiments, the hydrophobic material is selected from materials such as hydroxyalkylcelluloses such as hydroxypropylmethylcellulose and mixtures of the foregoing.

Preferred hydrophobic materials are water-insoluble with more or less pronounced hydrophilic and/or hydrophobic trends. Preferably, the hydrophobic materials useful in the invention have a melting point from about 30° to about 200° C., preferably from about 450° C. to about 90° C. Specifically, the hydrophobic material may comprise natural or synthetic waxes, fatty alcohols (such as lauryl, myristyl, stearyl, cetyl or preferably cetostearyl alcohol), fatty acids, including but not limited to fatty acid esters, fatty acid glycerides (mono-, di-, and tri-glycerides), hydrogenated fats, hydrocarbons, normal waxes, stearic aid, stearyl alcohol and hydrophobic and hydrophilic materials having hydrocarbon backbones. Suitable waxes include, for example, beeswax, glycowax, castor wax and carnauba wax. For purposes of the present invention, a wax-like substance is defined as any material which is normally solid at room temperature and has a melting point of from about 30° to about 100° C.

Suitable hydrophobic materials which may be used in accordance with the present invention include digestible, long chain ($C_8$–$C_{50}$, especially $C_{12}$–$C_{40}$), substituted or unsubstituted hydrocarbons, such as fatty acids, fatty alcohols, glyceryl esters of fatty acids, mineral and vegetable oils and natural and synthetic waxes. Hydrocarbons having a melting point of between 25° and 90° C. are preferred. Of the long chain hydrocarbon materials, fatty (aliphatic) alcohols are preferred in certain embodiments. The oral dosage form may contain up to 60% (by weight) of at least one digestible, long chain hydrocarbon.

Preferably, a combination of two or more hydrophobic materials are included in the matrix formulations. If an additional hydrophobic material is included, it is preferably selected from natural and synthetic waxes, fatty acids, fatty alcohols, and mixtures of the same. Examples include beeswax, carnauba wax, stearic acid and stearyl alcohol. This list is not meant to be exclusive.

One particular suitable matrix comprises at least one water soluble hydroxyalkyl trig cellulose, at least one $C_{12}$–$C_{36}$, preferably $C_{14}$–$C_{22}$, aliphatic alcohol and, optionally, at least one polyalkylene glycol. The at least one hydroxyalkyl cellulose is preferably a hydroxy ($C_1$ to $C_6$) alkyl cellulose, such as hydroxypropylcellulose, hydroxypropylmethylcellulose and, especially, hydroxyethylcellulose. The amount of the at least one hydroxyalkyl cellulose in the present oral dosage form will be determined, inter alia, by the precise rate of opioid release required. The at least one aliphatic alcohol may be, for example, lauryl alcohol, myristyl alcohol or stearyl alcohol. In particularly preferred embodiments of the present oral dosage form, however, the at least one aliphatic alcohol is cetyl alcohol or cetostearyl alcohol. The amount of the at least one aliphatic alcohol in the present oral dosage form will be determined, as above, by the precise rate of opioid release required. It will also depend on whether at least one polyalkylene glycol is present in or absent from the oral dosage form. In the absence of at least one polyalkylene glycol, the oral dosage form preferably contains between 20% and 50% (by wt) of the at least one aliphatic alcohol. When at least one polyalkylene glycol is present in the oral dosage form, then the combined weight of the at least one aliphatic alcohol and the at least one polyalkylene glycol preferably constitutes between 20% and 50% (by wt) of the total dosage.

In one embodiment, the ratio of, e.g., the at least one hydroxyalkyl cellulose or acrylic resin to the at least one aliphatic alcohol/ polyalkylene glycol determines, to a considerable extent, the release rate of the opioid from the formulation. A ratio of the at least one hydroxyalkyl cellulose to the at least one aliphatic alcohol/polyalkylene glycol of between 1:2 and 1:4 is preferred, with a ratio of between 1:3 and 1:4 being particularly preferred.

The at least one polyalkylene glycol may be, for example, polypropylene glycol or, which is preferred, polyethylene glycol. The number average molecular weight of the at least one polyalkylene glycol is preferred between 1,000 and 15,000 especially between 1,500 and 12,000.

Another suitable controlled release matrix would comprise an alkylcellulose (especially ethyl cellulose), a $C_{12}$ to $C_{36}$ aliphatic alcohol and, optionally, a polyalkylene glycol.

In another preferred embodiment, the matrix includes a pharmaceutically acceptable combination of at least two hydrophobic materials.

In addition to the above ingredients, a controlled release matrix may also contain suitable quantities of other materials, e.g. diluents, lubricants, binders, granulating aids, colorants, flavorants and glidants that are conventional in the pharmaceutical art.

Processes for Preparing Matrix—Based Beads

In order to facilitate the preparation of a solid, controlled release, oral dosage form according to this invention, any method of preparing a matrix formulation known to those skilled in the art may be used. For example incorporation in the matrix may be effected, for example, by (a) forming granules comprising at least one water soluble hydroxyalkyl cellulose and opioid or an opioid salt; (b) mixing the hydroxyalkyl cellulose containing granules with at least one $C_{12}$–$C_{36}$ aliphatic alcohol; and (c) optionally, compressing and shaping the granules. Preferably, the granules are formed by wet granulating the hydroxyalkyl cellulose/opioid with water. In a particularly preferred embodiment of this process, the amount of water added during the wet granulation step is preferably between 1.5 and 5 times, especially between 1.75 and 3.5 times, the dry weight of the opioid.

In yet other alternative embodiments, a spheronizing agent, together with the active ingredient can be spheronized to form spheroids. Microcrystalline cellulose is preferred. A suitable microcrystalline cellulose is, for example, the material sold as Avicel PH 101 (Trade Mark, FMC Corporation). In such embodiments, in addition to the active ingredient and spheronizing agent, the spheroids may also contain a binder. Suitable binders, such as low viscosity, water soluble polymers, will be well known to those skilled in the pharmaceutical art. However, water soluble hydroxy lower alkyl cellulose, such as hydroxypropylcellulose, are preferred. Additionally (or alternatively) the spheroids may contain a water insoluble polymer, especially an acrylic polymer, an acrylic copolymer, such as a methacrylic acid-ethyl acrylate copolymer, or ethyl cellulose. In such embodiments, the sustained release coating will generally include a hydrophobic material such as (a) a wax, either alone or in admixture with a fatty alcohol; or (b) shellac or zein.

Melt Extrusion Matrix

Sustained release matrices can also be prepared via melt-granulation or melt-extrusion techniques. Generally, melt-granulation techniques involve melting a normally solid hydrophobic material, e.g. a wax, and incorporating a powdered drug therein. To obtain a sustained release dosage form, it may be necessary to incorporate an additional hydrophobic substance, e.g. ethylcellulose or a water-insoluble acrylic polymer, into the molten wax hydrophobic material. Examples of sustained release formulations prepared via melt-granulation techniques are found in U.S. Pat. No, 4,861,598, assigned to the Assignee of the present invention and hereby incorporated by reference in its entirety.

The additional hydrophobic material may comprise one or more water-insoluble wax-like thermoplastic substances possibly mixed with one or more wax-like thermoplastic substances being less hydrophobic than said one or more water-insoluble wax-like substances. In order to achieve constant release, the individual wax-like substances in the formulation should be substantially non-degradable and insoluble in gastrointestinal fluids during the initial release phases. Useful water-insoluble wax-like substances may be those with a water-solubility that is lower than about 1:5,000 (w/w).

In addition to the above ingredients, a sustained release matrix may also contain suitable quantities of other materials, e.g., diluents, lubricants, binders, granulating aids, colorants, flavorants and glidants that are conventional in the pharmaceutical art. The quantities of these additional materials will be sufficient to provide the desired effect to the desired formulation. In addition to the above ingredients, a sustained release matrix incorporating melt-extruded multiparticulates may also contain suitable quantities of other materials, e.g. diluents, lubricants, binders, granulating aids, colorants, flavorants and glidants that are conventional in the pharmaceutical art in amounts up to about 50% by weight of the particulate if desired.

Specific examples of pharmaceutically acceptable carriers and excipients that may be used to formulate oral dosage forms are described in the *Handbook of Pharmaceutical Excipients*, American Pharmaceutical Association (1986), incorporated by reference herein.

Melt Extrusion Multiparticulates

The preparation of a suitable melt-extruded matrix according to the present invention may, for example, include the steps of blending the opioid analgesic, together with at least one hydrophobic material and preferably the additional hydrophobic material to obtain a homogeneous mixture. The homogeneous mixture is then heated to a temperature sufficient to at least soften the mixture sufficiently to extrude the same. The resulting homogeneous mixture is then extruded to form strands. The extrudate is preferably cooled and cut into multiparticulates by any means known in the art. The strands are cooled and cut into multiparticulates. The multiparticulates are then divided into unit doses. The extrudate preferably has a diameter of from about 0.1 to about 5 mm and provides sustained release of the therapeutically active agent for a time period of from about 8 to about 24 hours.

An optional process for preparing the melt extrusions of the present invention includes directly metering into an extruder a hydrophobic material, a therapeutically active agent, and an optional binder; heating the homogenous mixture; extruding the homogenous mixture to thereby form strands; cooling the strands containing the homogeneous mixture; cutting the strands into particles having a size from about 0.1 mm to about 12 mm; and dividing said particles into unit doses. In this aspect of the invention, a relatively continuous manufacturing procedure is realized.

The diameter of the extruder aperture or exit port can also be adjusted to vary the thickness of the extruded strands. Furthermore, the exit part of the extruder need not be round; it can be oblong, rectangular, etc. The exiting strands can be reduced to particles using a hot wire cutter, guillotine, etc.

The melt extruded multiparticulate system can be, for example, in the form of granules, spheroids or pellets depending upon the extruder exit orifice. For purposes of the present invention, the terms "melt-extruded multiparticulate (s)" and "melt-extruded multiparticulate system(s)" and "melt-extruded particles" shall refer to a plurality of units, preferably within a range of similar size and/or shape and containing one or more active agents and one or more excipients, preferably including a hydrophobic material as described herein. In this regard, the melt-extruded multiparticulates will be of a range of from about 0.1 to about 12 mm in length and have a diameter of from about 0.1 to about 5 mm. In addition, it is to be understood that the melt-extruded multiparticulates can be any geometrical shape within this size range. Alternatively, the extrudate may simply be cut into desired lengths and divided into unit doses of the therapeutically active agent without the need of a spheronization step.

In one preferred embodiment, oral dosage forms are prepared to include an effective amount of melt-extruded multiparticulates within a capsule. For example, a plurality of the melt-extruded multiparticulates may be placed in a gelatin capsule in an amount sufficient to provide an effective sustained release dose when ingested and contacted by gastric fluid.

In another preferred embodiment, a suitable amount of the multiparticulate extrudate is compressed into an oral tablet using conventional tableting equipment using standard techniques. Techniques and compositions for making tablets (compressed and molded), capsules (hard and soft gelatin) and pills are also described in *Remington's Pharmaceutical Sciences,* (Arthur Osol, editor), 1553–1593 (1980), incorporated by reference herein.

In yet another preferred embodiment, the extrudate can be shaped into tablets as set forth in U.S. Pat. No. 4,957,681 (Klimesch, et. al.), described in additional detail above and hereby incorporated by reference.

Optionally, the sustained release melt-extruded multiparticulate systems or tablets can be coated, or the gelatin capsule can be further coated, with a sustained release coating such as the sustained release coatings described above. Such coatings preferably include a sufficient amount of hydrophobic material to obtain a weight gain level from about 2 to about 30 percent, although the overcoat may be greater depending upon the physical properties of the particular opioid analgesic compound utilized and the desired release rate, among other things.

The melt-extruded unit dosage forms of the present invention may further include combinations of melt-extruded multiparticulates containing one or more of the therapeutically active agents disclosed above before being encapsulated. Furthermore, the unit dosage forms can also include an amount of an immediate release therapeutically active agent for prompt therapeutic effect. The immediate release therapeutically active agent may be incorporated, e.g., as separate pellets within a gelatin capsule, or may be coated on the surface of the multiparticulates after preparation of the dosage forms (e.g., controlled release coating or matrix-based). The unit dosage forms of the present invention may also contain a combination of controlled release beads and matrix multiparticulates to achieve a desired effect.

The sustained release formulations of the present invention preferably slowly release the therapeutically active agent, e.g., when ingested and exposed to gastric fluids, and then to intestinal fluids. The sustained release profile of the melt-extruded formulations of the invention can be altered, for example, by varying the amount of retardant, i.e., hydrophobic material, by varying the amount of plasticizer relative to hydrophobic material, by the inclusion of additional ingredients or excipients, by altering the method of manufacture, etc.

In other embodiments of the invention, the melt extruded material is prepared without the inclusion of the therapeutically active agent, which is added thereafter to the extrudate. Such formulations typically will have the therapeutically active agent blended together with the extruded matrix material, and then the mixture would be tableted in order to provide a slow release formulation. Such formulations may be advantageous, for example, when the therapeutically active agent included in the formulation is sensitive to temperatures needed for softening the hydrophobic material and/or the retardant material.

Detailed Description of Preferred Embodiments

The following examples illustrate various aspects of the present invention. They are not to be construed to limit the claims in any manner whatsoever.

EXAMPLE 1

The separability of Naltrexone Hydrochloride from Hydrocodone Bitartrate using an extraction procedure mimicking that of a drug abuser is examined. Inspection of the structures and consideration of the pKa's (FIG. 1) would suggest that both compounds would be soluble in acid. However, Naltrexone should also be very soluble at high pH's with a minimum solubility between pH 8.4 and 10.3. We wanted to test the hypothesis that both compounds could be extracted from a tablet in acid and then the Hydrocodone could be precipitated out by high pH.

Since Hydrocodone controlled release tablets (HYCR) and Naltrexone tablets were not available for this study, simulated samples were prepared by adding known amounts of Hydrocodone Bitartrate and Naltrexone Hydrochloride drug substances to HYCR AcroContin 15 mg tablets placebo ("Acrocontin" refers to a proprietary controlled release base comprising an ammonio methacrylate polymer together with a higher aliphatic alcohol, as described for example in U.S. Pat. No. 4,861,598, hereby incorporated by reference) Different solvents of varying pH's were used to extract Hydrocodone Bitartrate and/or Naltrexone HCl at concentrations of 4 tablets/25 mL (section 2.1) and 5 tablets/5 ML (section 2.2) of solvent. The recoveries were quantitated using HPLC.

2.1 Extraction at Concentrations of 4 Tablets in 25 mL of Solvent 2.1.1 About 60 mg of Hydrocodone bitartrate, 25 mg of Naltrexone hydrochloride and 400 mg of HYCR 15 mg AcroContin tablets placebo (equivalent to 4 tablets) were added to a 25 mL volumetric flask. About 15 mL of water was added into the volumetric flask and the solution was sonicated for 10 minutes. The solution was diluted to volume with water and mixed well. This was the sample stock solution. Thirteen sample stock solutions were prepared in this manner.

2.1.2 The pH of the solutions were then adjusted with either glacial acetic acid or 0.2N NaOH to pH 2.0, 4.0, 5.1, 6.0, 6.5, 7.0, 7.4, 8.0, 8,5, 9.0, 9,4, and 10.0. However, in preparing the pH 1.1 solution, hydrochloric acid was used. Then step 2.1.4. was followed.

2.1.3 Step 2.1.1 of the procedure was repeated to prepare sample stock solutions in ethanol, methanol and acetone instead of water.

2.1.4 Each solution was filtered using a 5 mL disposable syringe and a Millex-HV 0.45 μm filter unit. 1.0 mL of the clear filtrate was pipetted into a 25 mL volumetric flask, diluted to volume with water and mixed well. The sample solutions were then injected onto the HPLC system and the results are presented in Table 1.

2.2 Extraction at Concentrations of 5 Tablets in 5 mL of Solvent 2.2.1 About 75 mg of Hydrocodone bitartrate and 32 mg of Naltrexone hydrochloride were added to a scintillation vial which contained 475 mg of HYCR 15 mg AcroContin tablets placebo (equivalent to 5 tablets). 5.0 mL of water was added into the scintillation via and the solution was sonicated for 10 minutes. This was the sample stock solution.

2.2.2 The solution's pH was then adjusted with 50% w/w NaOH to pH 7.1. After the solution settled for one hour, the entire solution was filtered using a 5 mL disposable syringe and a Millex-HV 0.45 μm filter unit. 1.0 mL of this clear filtrate was pipetted into a 25 mL volumetric flask, diluted to volume with water, and mixed well. This was the pH 7.1 sample stock solution.

2.2.3 Steps 2.2.1 and 2.2.2 of the procedure was repeated to prepare the sample solutions at pH 8.0, 9.0, 10.0, 11.0, 12.0 and 12.7. The samples solutions were then injected onto the HPLC system and the results are present in Table 2.

3. Results

The results are presented in Table 1 and 2. In Table 2, it is noted that both Hydrocodone and Naltrexone dissolved completely in all of the solvents except acetone. In Table 2, it is noted that the amount of Naltrexone retained in the solution decreased at pH 8 and increased again at pH 10 and the Hydrocodone retained in the solution decreased at higher pH.

TABLE 1

Simulated Exractability of Naltrexone Hydrochloride from Hydrocodone Bitartrate CR 15 mg AcroContin Tablets at Concentration of 4 Tablets in 25 mL of Solvent.

| | | % Recovery | |
|---|---|---|---|
| Sample # | Diluent | Naltrexone | Hydrocodone |
| 1 | pH 1.1 | 101 | 101 |
| 2 | pH 3.0 | 102 | 101 |
| 3 | pH 4.0 | 100 | 100 |
| 4 | pH 5.1 | 102 | 100 |
| 5 | pH 6.0 | 102 | 100 |
| 6 | pH 6.5 | 99 | 99 |
| 7 | pH 7.0 | 100 | 100 |
| 8 | pH 7.4 | 100 | 101 |
| 9 | pH 8.0 | 102 | 99 |
| 10 | pH 8.5 | 99 | 100 |
| 11 | pH 9.0 | 99 | 99 |
| 12 | pH 9.4 | 100 | 100 |
| 13 | pH 10.0 | 97 | 99 |
| 14 | Ethanol | 116 | 89 |
| 15 | Methanol | 106 | 102 |
| 16 | Acetone | 35 | 21 |

TABLE 2

Simulated Exractability of Naltrexone Hydrochloride from Hydrocodone Bitartrate CR 15 mg AcroContin Tablets at Concentration of 5 Tablets in 5 mL of Solvent.

| | | % Recovery | | % Precipitated |
|---|---|---|---|---|
| Sample # | Diluent | Naltrexone | Hydrocodone | Hydrocodone |
| 1 | pH 7.1 | 92 | 92 | 8 |
| 2 | pH 8.0 | 84 | 88 | 12 |
| 3 | pH 9.0 | 46 | 73 | 27 |
| 4 | pH 10.0 | 49 | 72 | 28 |
| 5 | pH 11.0 | 70 | 79 | 21 |

TABLE 2-continued

Simulated Exractability of Naltrexone Hydrochloride from
Hydrocodone Bitartrate CR 15 mg AcroContin Tablets at
Concentration of 5 Tablets in 5 mL of Solvent.

| | | % Recovery | | % Precipitated |
|---|---|---|---|---|
| Sample # | Diluent | Naltrexone | Hydrocodone | Hydrocodone |
| 6 | pH 12.0 | 88 | 17 | 83 |
| 7 | pH 12.7 | 87 | 19 | 81 |

FIG. 1 provides structures and pKa Values of Hydrocodone and Naltrexone Base.

4. Conclusions

In Table 1, it can be observed that the concentrations of Hydrocodone and Naltrexone were too low in 25 mL of solvents and they dissolved almost completely in varying pH's as well as in ethanol and methanol. In acetone, Hydrocodone and Naltrexone are less soluble and poor recoveries were obtained.

In Table 2, the results can be explained by examining the pKa's of the drug substances. The pKa values of Naltrexone Hydrochloride which were obtained in PRC, Yonkers are 8.4 (at amine functional group) and 10.3 (at phenol functional group) and the pKa value of Hydrocodone Bitartrate (at amine functional group) is 9.2. The chemical structures and pKa values of Hydrocodone and Naltrexone base are shown in FIG. 1.

For Naltrexone Hydrochloride: As the pH reaches 8.4, the Naltrexone becomes the free base form and starts precipitating out of the solution and when the pH reaches 10.3, the phenolic OH functional group deionizes and the compound dissolves again into the solution. For Hydrocodone Bitartrate: The Hydrocodone becomes free base at pH higher than 9.2 and starts to precipitate out of the solution.

Table 1 shows that about 80% of Hydrocodone Bitartrate and 10% of Naltrexone Hydrochloride might be extractable from the tablets at the higher pH's.

This procedure would probably not be that easy on the street. Both strong acid and strong base would be required plus grinding and filtering steps. Moreover, the recovered hydrocodone is soaked with strong caustic, any attempt to wash off the caustic would result in some loss of hydrocodone.

However, it is important to note that in this wet recovery experiment, neither drug was incorporated into the tablet matrix through the manufacturing procedure (hot wax). It is most likely that from an actual tablet the recoveries could be worse. Additionally, the addition of a gelling agent or other excipients could make it even more difficult.

EXAMPLE 2

Extractability of Nalterexone Hydrochloride (1.5 mg) from Hydromorphone Hydrochoride (15 mg) at a concentration of 5 tablets/5 mL of solvent is studied, using the same techniques set forth in Example 1. The results are provided in Table 3 below:

TABLE 3

| | | % Recovery | | % Precipitated Hydromorphone |
|---|---|---|---|---|
| Sample # | Diluent | Naltrexone | Hydromorphone | |
| 1 | pH 7.2 | 95 | 95 | 5 |
| 2 | pH 7.9 | 88 | 91 | 9 |
| 3 | pH 9.0 | 79 | 90 | 10 |
| 4 | pH 9.9 | 79 | 90 | 10 |
| 5 | pH 11.0 | 79 | 89 | 11 |
| 6 | pH 11.9 | 84 | 88 | 12 |
| 7 | pH 12.9 | 69 | 73 | 27 |
| 8 | Methanol | 96 | 66 | 34 |
| 9 | Ethanol | 97 | 32 | 68 |
| 10 | IPA | 90 | 1 | 99 |

EXAMPLE 3

The extractability of Nalterexone Hydrochloride (1.5 mg) from Oxycodone Hydrochoride (15 mg) at a concentration of 5 tablets/5 mL of solvent is studied, using the same techniques set forth in Example 1. The results are provided in Table 4 below:

TABLE 4

| | | % Recovery | | % Precipitated |
|---|---|---|---|---|
| Sample # | Diluent | Naltrexone | Oxycodone | Oxycodone |
| 1 | pH 6.9 | 101 | 94 | 6 |
| 2 | pH 8.1 | 80 | 13 | 87 |
| 3 | pH 9.4 | 62 | 2 | 98 |
| 4 | pH 10.2 | 58 | 2 | 98 |
| 5 | pH 11.0 | 78 | 2 | 98 |
| 6 | pH 11.9 | 68 | 2 | 98 |
| 7 | pH 12.8 | 76 | 2 | 98 |
| 8 | Methanol | 78 | 87 | 13 |
| 9 | Ethanol | 74 | 87 | 13 |
| 10 | IPA | 70 | 14 | 86 |

While the invention has been described and illustrated with reference to certain preferred embodiments thereof, those skilled in the art will appreciate that obvious modifications can be made herein without departing from the spirit and scope of the invention. Such variations are contemplated to be within the scope of the appended claims.

What is claimed is:

1. A method of reducing the abuse potential of a sustained release oral dosage form of an opioid analgesic, comprising
   combining an analgesically effective amount of an orally active opioid agonist together with an opioid antagonist and a sustained release carrier into an oral dosage form;
   said dosage form providing a release of said opioid analgesic for about 12 to about 24 hours;
   said opioid agonist/antagonist combination being chosen such that the opioid agonist and opioid antagonist are only extractable from the dosage form together, and at least a two-step extraction process is required to separate the opioid antagonist from the opioid agonist, the amount of opioid antagonist included being sufficient to counteract opioid effects if extracted together from the oral dosage form together with the opioid agonist and administered parenterally.

2. The method of claim 1, wherein said combination of said opioid agonist and said opioid antagonist are only extractable from the dosage form together, and thereafter must be separated from each other in a separate extraction step.

3. The method of claim 2, wherein both said opioid agonist and said opioid antagonist are soluble in acid, and must be separated utilizing a high pH solution.

4. The method of claim 3, wherein said opioid agonist is hydrocodone bitartrate and said opioid antagonist is naltrexone hydrochloride, wherein both the hydrocodone and naltrexone dissolve at a pH less than 8 and about 80% of said hydrocodone and about 10% of said naltrexone are extractable at a high pH.

5. The method of claim 1 where the opioid agonist is hydromorphone hydrochloride and the opioid antagonist is naltrexone hydrochloride.

6. The method of claim 1 where the opioid agonist is oxycodone hydrochloride and the opioid antagonist is naltrexone hydrochloride.

7. The method of claim 1 where the opioid agonist is morphine sulfate and the opioid antagonist is naltrexone hydrochloride.

8. The method of claim 3, further comprising incorporating into the dosage form a further ingredient which makes separation of the opioid agonist from the opioid antagonist more difficult.

9. The method of claim 8, wherein said further ingredient is selected from the group consisting of gelling agents, waxes, and mixtures thereof.

10. The method of claim 8, further comprising incorporating into the preparation of the dosage form one or more processing steps which further impede the separation of the opioid agonist from the opioid antagonist.

11. The method of claim 1, wherein said opioid antagonist is naltrexone or a pharmaceutically acceptable salt thereof, said opioid agonist is hydromorphone or a pharmaceutically acceptable salt thereof, and the ratio of said naltrexone to said hydromorphone is from about 0.222:1 to about 0.889:1 by weight.

12. The method of claim 1, wherein said opioid antagonist is naltrexone or a pharmaceutically acceptable salt thereof, said opioid agonist is oxycodone or a pharmaceutically acceptable salt thereof, and the ratio of said naltrexone to said oxycodone is from about 0.037:1 to about 0.296:1 by weight.

13. The method of claim 1, wherein said opioid antagonist is naltrexone or a pharmaceutically acceptable salt thereof, said opioid agonist is oxycodone or a pharmaceutically acceptable salt thereof, and the ratio of said naltrexone to said oxycodone is from about 0.056:1 to about 0.222:1 by weight.

14. The method of claim 1, wherein said opioid antagonist is naltrexone or a pharmaceutically acceptable salt thereof, said opioid agonist is morphine or a pharmaceutically acceptable salt thereof, and the ratio of said naltrexone to said morphine is from about 0.018:1 to about 0.148:1 by weight.

15. The method of claim 1, wherein said opioid antagonist is naltrexone or a pharmaceutically acceptable salt thereof, said opioid agonist is morphine or a pharmaceutically acceptable salt thereof, and the ratio of said naltrexone to said morphine is from about 0.028:1 to about 0.111:1 by weight.

16. The method of claim 1, wherein said opioid antagonist is naltrexone or a pharmaceutically acceptable salt thereof, said opioid agonist is hydrocodone or a pharmaceutically acceptable salt thereof, and the ratio of said naltrexone to said hydrocodone is from about 0.03:1 to about 0.27:1 by weight.

17. The method of claim 1, wherein said opioid antagonist is naltrexone or a pharmaceutically acceptable salt thereof, said opioid agonist is hydrocodone or a pharmaceutically acceptable salt thereof, and the ratio of said naltrexone to said hydrocodone is from about 0.05:1 to about 0.20:1 by weight.

18. The method of claim 1, wherein said opioid antagonist is naltrexone or a pharmaceutically acceptable salt thereof.

19. The method of claim 1, wherein said opioid antagonist causes said opioid agonist/antagonist combination to provide an aversive effect in a physically dependent human subject when the sustained release oral dosage form is orally administered.

20. The method of claim 1, wherein said opioid agonist and opioid antagonist are incorporated in a matrix formulation.

21. The method of claim 20, wherein said sustained release carrier is incorporated in said matrix formulation with said opioid agonist and opioid antagonist.

22. The method of claim 20, wherein said sustained release carrier is coated onto said matrix formulation.

23. The method of claim 20, wherein said sustained release carrier is incorporated in said matrix formulation with said opioid agonist and is coated onto said matrix formulation.

* * * * *